United States Patent
Lee et al.

(10) Patent No.: US 7,514,586 B2
(45) Date of Patent: Apr. 7, 2009

(54) ORGANIC ZINC PRECURSOR AND ZNO THIN-FILM DEPOSITION BY MOCVD

(75) Inventors: Chrong-Ching Lee, Hsinchu (TW); Ren-Bor Lin, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 653 days.

(21) Appl. No.: 11/107,834

(22) Filed: Apr. 18, 2005

(65) Prior Publication Data

US 2006/0198957 A1    Sep. 7, 2006

(30) Foreign Application Priority Data

Mar. 3, 2005    (TW)    ............... 94106446 A

(51) Int. Cl.
    *C07F 15/00*    (2006.01)
(52) U.S. Cl. ............... 568/300; 427/248.1; 427/255.28; 427/162; 427/157; 427/64; 427/58
(58) Field of Classification Search .............. 427/248.1
    See application file for complete search history.

(56) References Cited

OTHER PUBLICATIONS

Suzuki et al., The Reation of Bivalent Transition Metal Acetylacetonates with Ethylene Glycol and the Catalytic Effect of the Reaction Products on the Transesterification between Dimethyl Terepthalate and Ethylene Glycol, 1976, Nippon Kagaku Kaishi, 663-9.*

* cited by examiner

*Primary Examiner*—Michael Barr
*Assistant Examiner*—Andrew Bowman
(74) *Attorney, Agent, or Firm*—Bacon & Thomas, PLLC

(57) ABSTRACT

The present invention discloses an organic zinc precursor for depositing an zinc oxide layer on a substrate by metal organic chemical vapor deposition (MOCVD), which is a zinc-ligand complex having the following formula:

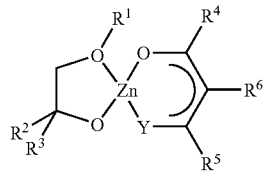

wherein Y is O or $NR^7$; $R^1$, $R^2$ and $R^3$ independently are H, halogen, $C_{1-8}$ alkyl, $C_{1-8}$ haloalkyl, aryl or haloaryl; $R^4$, $R^5$ and $R^7$ independently are $C_{1-8}$ alkyl, $C_{1-8}$ haloalkyl, aryl or haloaryl; $R^6$ is H, halogen, $C_{1-8}$ alkyl or $C_{1-8}$ haloalkyl.

8 Claims, 1 Drawing Sheet

ORGANIC ZINC PRECURSOR AND ZNO THIN-FILM DEPOSITION BY MOCVD

FIELD OF THE INVENTION

The present invention relates to a method for synthesizing a novel organic zinc precursor and a technique of using said precursor to form a ZnO thin-film on a substrate by Metal Oxide Chemical Vapor Deposition (MOCVD).

BACKGROUND OF THE INVENTION

Zinc oxide (ZnO) is a typical Group II-VI semiconductor material and is a compound with a direct wide-band gap (3.37 eV). It has excellent optical and electrical properties, and great conditions for emitting blue light or near ultraviolet light. Thus, zinc oxide has the potential in the development of a variety of light emitting devices emitting ultraviolet light, green light, or blue light, etc. Semiconductor photoelectric devices made from zinc oxide mainly include: ultraviolet detector, light emitting device (LED), and semiconductor laser device (LD), etc. Furthermore, an inorganic piezoelectric thin film made from nano zinc oxide can be used to produce an ultra-thin bulk acoustic device. Moreover, a ZnO thin-film sensor has the following advantages: rapid response, high degree of integration, low power consumption, high sensitivity, good selectivity, and cheap raw material, etc.

Generally, there are two types of process in carrying out ZnG thin-film deposition: one is solution chemical deposition, and the other is vapor deposition. The solution chemical deposition process includes a sol-gel process and a metal-organic decomposition process. The vapor deposition process includes a physical vapor deposition (PVD) process and a chemical vapor deposition (CVD) process. A CVD process comprises vaporizing a compound containing zinc, and depositing ZnO on a substrate. However, the vaporization step requires a rather high temperature. Therefore, later on a different deposition technique is developed using an organic metal complex precursor as raw material for reducing the vaporization temperature. Such a deposition technique is called a Metal Organic Chemical Vapor Deposition (MOCVD) technique. A MOCVD can be used to deposit thin films for dielectric material, conductor, or semiconductor, and includes the following advantages: good control in atomic quantitative ratio among different elements, larger area size matching, good film uniformity, good smoothness in step coverage, and high deposition rate, etc.

U.S. Pat. No. 4,751,149 discloses a method for deposition of a zinc film in a relatively low temperature environment, and also discloses a process for reducing the resistance of a zinc film by adding various additives. This prior art invention uses an alkyl zinc as a CVD precursor to grow a ZnO thin-film, in which the deposition temperature is about 200° C. and the thin-film resistivity is $10^{-4} \sim 10^{-2}$.

U.S. Pat. No. 6,416,814 discloses novel Sn and Zn ligand complexes, $MX_nL_2$, which can be used as CVD precursors. Said precursors have high reactive activities in a CVb process, while maintaining a high deposition film quality. Said $MX_nL_2$ are $SnCl_4L_2$ or $ZnR_2L_2$, wherein L is a ligand, e.g. methylformate, ethylformate, n-propylformate, n-butylformate, i-butylformate, t-butylformate or a mixture thereof; R is $C_{1-8}$ alkyl or $C_{2-8}$ alkenyl.

Metal ligand complex precursors for CVD usually use some bi-dentate ligands, e.g. acac (acetylacetone), thd (2,2,6,6-tetramethylheptane-3,5-dionate), thme (tris(hydroxymethyl)ethane), tdh (1,1,1,6,6,6-hexamethylheptane-2,4-dione), and fluoro-containing β-diketonate such as hfa (1,1,1,5,5,5-hexafluoro-2,4-pentanedione) and fod (2,2-diethyl-6,6,7,7,8,8,8-heptafluoro-3,5-octanedione). Fluoro contained in the ligand is for increasing the volatility of the precursor. However, many microelectronic processes do not permit the presence of halogen, such as fluorine. U.S. Pat. No. 6,099,903 discloses a novel ligand structure as shown in the following formula, wherein Y and Z separately are O, S or $NR^9$:

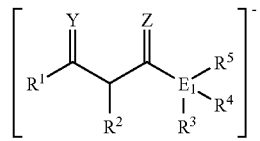

wherein the definitions of $R^1, R^2, R^3, R^4, R^5, R^9$ and $E^1$ can be found in said patent.

The disclosures in the above-mentioned US patents are incorporated herein by references.

SUMMARY OF THE INVENTION

A primary objective of the present invention is to provide a Zn-ligand complex, which can be used as an organic zinc precursor for deposition of ZnO thin-film on a substrate.

Another objective of the present invention is to provide a method for deposition of ZnO thin-film on a substrate by MOCVD.

A Zn-ligand complex disclosed in the present invention is shown by the following chemical structure (I):

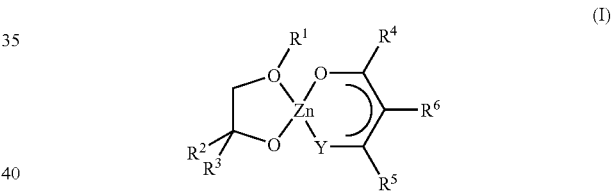

(I)

wherein Y is O or $NR^7$; wherein $R^1, R^2$ and $R^3$ independently are H, halogen, $C_{1-8}$ alkyl, halo-substituted $C_{1-8}$ alkyl, aryl, or halo-substituted aryl; $R^4, R^5$ and $R^7$ independently are $C_{1-8}$ alkyl, halo-substituted $C_{1-8}$ alkyl, aryl, or halo-substituted aryl; and $R^6$ is H, halogen, $C_{1-8}$ alkyl or halo-substituted $C_{1-8}$ alkyl.

Zn in the formula (I) can also be replaced by another transitional metal.

DETAILED DESCRIPTION OF THE INVENTION

Figure 1:
FIG. 1 to 4 show the SEM plan views of the ZnO thin-films deposited on four different substrates, Si(111), Si(100), ZnO buffer on Si(100), and a multi-layered Si substrate having a Si substrate, a $SiO_2$ layer on the substrate, a Ti layer on the $SiO_2$ layer, and a Pt layer on the Ti layer (Pt/Ti/$SiO_2$/Si), respectively.
Figure 2:
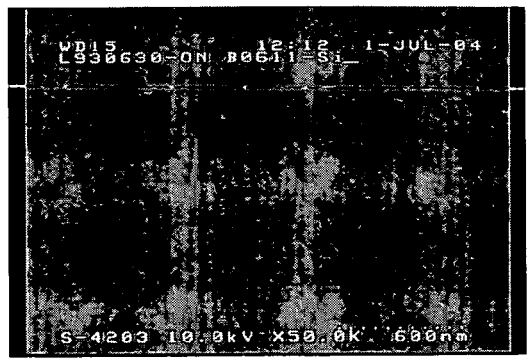
Figure 3:
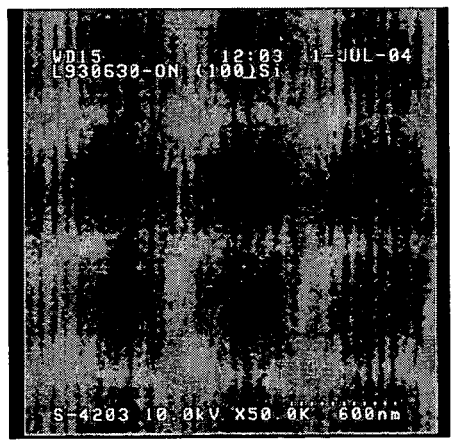
Figure 4:
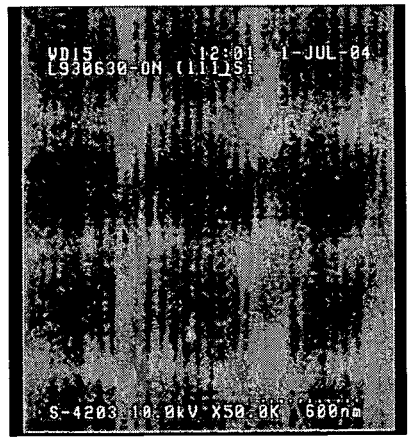

The present invention discloses a novel organic zinc precursor, and a method for deposition of ZnO thin-film on a substrate by MOCVD. According to one of the preferred embodiments of the present invention, an organic zinc precursor having the following chemical formula (M5) is synthesized:

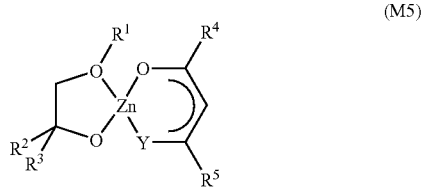

(M5)

wherein $R^1$, $R^2$, $R^3$, $R^4$ and $R^5$ are defined as above.

The organic zinc precursor M5 is a novel Zn-ligand complex containing a single zinc metal nucleus and two different ligands—one being a saturated alkyl oxy alkoxy ligand, $[R^1OCH_2C(R^2)(R^3)O]^-$, and the other being a β-diketonate ligand, $[R^4C(O)CHC(O)R^5]^-$. The two ligands chelate with one zinc atom to form the complex M5. In such a structure the ligands are bonded to the metal via oxygen, which is beneficial in reducing carbon residues during film deposition. The alkyl oxy alkoxy ligand provides the precursor with the reaction activity, and the β-diketonate ligand increases the molecular steric hindrance of the complex in order to reduce the molecule-molecule interactions and increase the volatility and stability, so that vapor of the complex M5 will not decompose upon entering the reaction chamber.

Most of the conventional metal-ligand complexes have a symmetrical structure, but a precursor according to the present invention has an asymmetrical structure.

The process of synthesizing the complex of the present invention is simple and stable. When $R^1$, $R^2$ and $R^3$ are methyl, and $R^4$ and $R^5$ are t-butyl, the complex M5 of the present invention has a melting point of about 130° C. at normal pressure, and a decomposition temperature of about 150° C. in air.

Without further elaboration, it is believed that the above description has adequately enabled the present invention. The following specific examples are, therefore, to be construed as merely illustrative, and not limitative of the remainder of the disclosure in any way whatsoever.

EXAMPLE 1

In this example, a Zn-ligand complex 1 was synthesized via the following reaction:

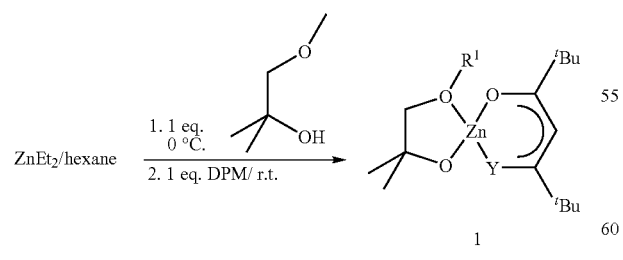

Into a 100 mL reaction bottle was prepared and, in a low temperature inert environment, hexane (20.0 mL) was added, then a 1.0 M $ZnEt_2$/hexane solution (10.0 mL) was added, and then $CH_3OCH_2C(CH_3)_2OH$ ligand (1.16 mL) was added. The resulting mixture was reacted at 0° C. for about 2 hours. Next, the resulting solution was added with DPM (dipivaloylmethane) (2.0 mL) at a low temperature, and the reaction was continued for 3 hours. Next, the solution was dried to obtain a white solid product 1 with a yield >98%.

$^1$H NMR, $C_6D_6$, 200 MHz: 5.84 (s, 1H), 3.06 (s, 3H), 2.94 (s, 2H), 1.23 (s, 18H), 1.11 (s, 6H).

The complex 1 was subjected to a thermogravimetric analysis (TGA) at a heating rate of 10° C./min, and the result indicates that the complex 1 has a thermal pyrolysis temperature of about 148° C. in air.

EXAMPLE 2

Figure 5:
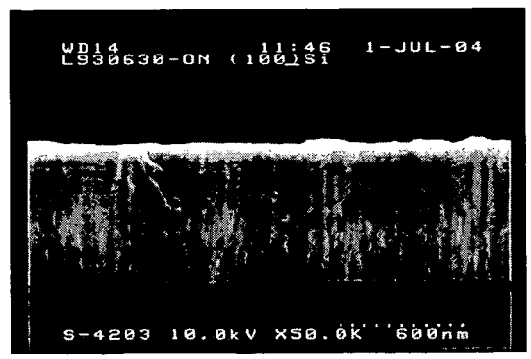
FIG. 5 show the SEM cross-sectional view of the ZnO thin-film deposited on the Si(100) substrate of the present invention.

The complex 1 synthesized in Example 1 was used to separately deposit a ZnO thin-film on various substrates using the conditions shown in the following table. FIG. 1 to 4 sequentially show the SEM plan views of the ZnO thin-films deposited on four different substrates Si(111), Si(100), ZnO buffer on Si(100), Pt/Ti/$SiO_2$/Si, respectively. FIG. 5 shows a SEM cross-sectional view of a ZnO thin-film deposited on a Si(100) substrate. The thickness of the ZnO thin-film shown in FIG. 5 is about 800 nm Furthermore, an EDX analysis (energy dispersive X-ray analysis) was carried out on the ZnO thin-film shown in FIG. 5, and the result indicates that the thin-film has singles of only Zn and O atoms and no signals of other elements, i.e. the thin-film deposited in this example is indeed a ZnO thin-film.

| | |
|---|---|
| Carrier gas | 500 sccm $N_2$ |
| CVD precursor material | 1.3 g complex 1 (liquid) |
| Reaction gas | 200 sccm $O_2$ |
| Temperature of the storage tank of the precursor | 170° C. |
| Temperature of the pipeline | 180° C. |
| Temperature of substrate | 500° C. |
| Deposition pressure | 10 torr |
| Deposition time | 3 hr |

An XRD analysis was conducted on the ZnO thin-films deposited on the four substrates, and the results indicate that the ZnO thin-film deposited on the Si(111) substrate has the strongest diffraction intensity, i.e. with best crystal phase.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

The invention claimed is:

1. A Zn-ligand complex having the following chemical structure (I):

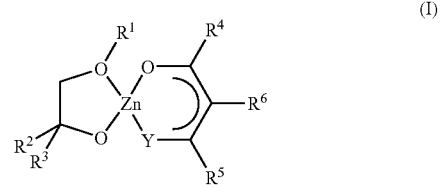

(I)

wherein Y is O or $NR^7$; $R^2$ and $R^3$ independently are H, halogen, $C_{1-8}$ alkyl, halo-$C_{1-8}$ alkyl, aryl or halo-aryl; $R^4$, $R^5$ and $R^7$ independently are $C_{1-8}$ alkyl, halo-$C_{1-8}$ alkyl, aryl or halo-aryl; and $R^6$ is H, halogen, $C_{1-8}$ alkyl or halo-$C_{1-8}$ alkyl; and $R^1$ is halogen, $C_{1-8}$ alkyl, halo-$C_{1-8}$ alkyl, aryl or halo-aryl.

2. The complex as claimed in claim 1, wherein Y is O; and $R^6$ is H or halogen.

3. The complex as claimed in claim 2, wherein $R^2$ and $R^3$ independently are H, halogen, $C_{1-8}$ alkyl or halo-$C_{1-8}$ alkyl; and $R^4$ and $R^5$ independently are $C_{1-8}$ alkyl or halo-$C_{1-8}$ alkyl.

4. The complex as claimed in claim 3, wherein $R^1$, $R^2$ and $R^3$ are methyl.

5. The complex as claimed in claim 4, wherein $R^4$ and $R^5$ independently are t-butyl or halo-methyl.

6. The complex as claimed in claim 5, wherein $R^4$ and $R^5$ are t-butyl.

7. The complex as claimed in claim 1, wherein Y is O, and $R^1$ is $C_{1-8}$ alkyl, halo-$C_{1-8}$ alkyl, aryl or halo-aryl.

8. The complex as claimed in claim 1, wherein Y is $NR^7$.

* * * * *